United States Patent [19]

Nicholson

[11] Patent Number: 4,952,142
[45] Date of Patent: * Aug. 28, 1990

[54] METHOD OF BONDING ORTHODONTIC BRACKETS

[76] Inventor: James Nicholson, 128 S. 28th Ave., Hattiesburg, Miss. 39401

[*] Notice: The portion of the term of this patent subsequent to Jun. 7, 2005 has been disclaimed.

[21] Appl. No.: 199,755

[22] Filed: May 27, 1988

Related U.S. Application Data

[63] Continuation-in-part of Ser. No. 691,101, Jan. 14, 1985, Pat. No. 4,749,352, which is a continuation-in-part of Ser. No. 632,931, Jul. 20, 1984, abandoned.

[51] Int. Cl.$^5$ ................................................. A61C 3/00
[52] U.S. Cl. ........................................... 433/9; 433/24
[58] Field of Search .................. 433/8, 9, 24; 523/116

[56] References Cited

U.S. PATENT DOCUMENTS

| | | | |
|---|---|---|---|
| 3,066,112 | 11/1962 | Bowen | 523/116 |
| 3,250,003 | 5/1966 | Collito | 433/9 |
| 3,709,866 | 1/1973 | Waller | 433/228.1 |
| 3,745,653 | 7/1973 | Cohl | 433/24 |
| 3,825,518 | 7/1974 | Foster | 433/228.1 |
| 3,949,477 | 4/1976 | Cohen et al. | 433/9 |
| 4,063,360 | 12/1977 | Waller | 433/9 |
| 4,089,763 | 5/1978 | Dert et al. | 433/228.1 |
| 4,179,812 | 12/1979 | White | 433/9 |
| 4,180,911 | 1/1980 | Bullock | 433/9 |
| 4,200,980 | 5/1980 | Johnston | 433/8 |
| 4,411,625 | 10/1983 | Koblitz et al. | 433/217 |
| 4,435,160 | 3/1984 | Randkler | 433/9 |
| 4,459,193 | 7/1984 | Ratcliffe et al. | 433/228.1 |
| 4,479,782 | 10/1984 | Orlowski et al. | 433/9 |
| 4,491,453 | 1/1985 | Koblitz et al. | 433/217 |
| 4,504,231 | 3/1985 | Koblitz et al. | 433/228.1 |
| 4,544,467 | 10/1985 | Bunker et al. | 433/222.1 |
| 4,801,528 | 1/1989 | Beppett | 433/220 |

FOREIGN PATENT DOCUMENTS 1428674 3/1976 United Kingdom .................... 433/9

Primary Examiner—John J. Wilson
Attorney, Agent, or Firm—Dowell & Dowell

[57] ABSTRACT

A method of direct or indirect bonding orthodontic brackets including metal, ceramic, sapphire, plastic and other clear brackets to teeth utilizing light curable polymer bonding agent compounds which are sufficiently viscous in an uncured state to retain a bracket in an applied position on the tooth until the bonding agent is cured and which bonding agents are curable within approximately twenty (20) seconds or less, by directing a visible and/or ultraviolet light source between the base of the bracket and the tooth to thereby thoroughly and securely bond the bracket to the tooth in the desired position. The method subsequently permits the bracket to be removed simultaneously with most of the bonding agent attached thereto thereby facilitating tooth cleaning following bracket removal.

9 Claims, 1 Drawing Sheet

METHOD OF BONDING ORTHODONTIC BRACKETS

REFERENCE TO RELATED APPLICATIONS

This application is a continuation-in-part application of applicant's copending application Ser. No. 691,101, filed Jan. 14, 1985, and now U.S. Pat. No. 4,749,352, which is a continuation-in-part application of Ser. No. 632,931 filed July 20, 1984, now abandoned, both entitled METHOD OF ORTHODONTIC BRACKETS.

BACKGROUND OF THE INVENTION

1. Field of the Invention

This invention is generally directed to a method of attaching orthodontic brackets to teeth and particularly to a method of direct or indirect bonding orthodontic brackets utilizing photopolymerizable bonding agent compounds having sufficient viscosity to retain a bracket in a desired position on the tooth after which a visible and/or ultraviolet light source is used to cure the polymers by directing the light from various angles between or relative to the base of a bracket and a tooth. The method is particularly adapted to permit bonding of brackets having solid or imperforate metal and ceramic or clear plastic or sapphire bases to teeth in less time than other known methods.

2. History of the Prior Art

Heretofore there have been various methods proposed for attaching orthodontic appliances to the surface of teeth. Many of the methods employed composites having somewhat lengthy setting times thereby requiring the orthodontist to retain a pressured grip on the orthodontic appliance or bracket during setting of the composite. Oftentimes, due to the long setting time, brackets would be shifted slightly and, therefore, not properly aligned when the composite began to set. Problems were also experienced in that excess composite would have to be removed from portions of the teeth adjacent the bracket which may have been coated by accidentally moving the bracket during its application. Such procedures were not efficient and required additional work for the orthodontist.

More recently, various polymers have been introduced which are more quickly cured. Many of these polymers may be subjected to heat, light or other radiant energy sources to induce a quick set of the polymer.

The problem encountered with use of some of the quick setting polymers has been that once the bracket has been coated with the polymer and placed against the tooth's surface, the polymer begins to cure so quickly that accurate bracket alignment is not always achieved. In such instances, the bracket must be removed from the tooth and the procedure repeated.

In the use of light or photo curable polymers, it has been necessary to enlarge the base of the orthodontic appliance or bracket and to make the base open or porous so that the polymer could be directly subjected or exposed through the holes or openings in the base to the waves of energy being used to polymerize the bonding agent. Absent the openings in the base of the brackets, it has heretofore been thought not possible to bond metallic or opaque bracket bases to teeth using a light curable polymer.

The use of larger bases for brackets not only results in an unattractive appearance but also increases the tooth surface are over which an orthodontic bracket is secured. Two problems are created by covering additional tooth surface. First, additional cleaning is necessary when the brackets are removed, and, second, there is an increased risk of damage to a larger area of a tooth's surface as the larger bracket bases make a greater area available in which food particles may be trapped increasing the likelihood of tooth decay in the area of the bracket.

A further problem with many prior art orthodontic bonding techniques has been that the brackets do not have sufficient bond strength to insure their placement over an extended period of time. Insufficient bond strength results in the necessity to replace various brackets during the course of a patient's treatment.

From the foregoing, it is obvious that orthodontists have been faced with several major problems. The first problem concerns the precise alignment of the brackets on the teeth which problem is directly affected by the length of time it takes the bonding agent to cure and the ability of the bonding agent to retain the bracket in a placed position prior to curing. Another problem directly concerns the failure of the bond between the bracket and the surface of a tooth. The need that various photopolymerizable bonding agents be visible or directly exposed through the base of the brackets to photo sources has presented a third problem in that known curing and bonding techniques have not been conducive to bond essentially any type of orthodontic brackets including imperforate and opaque brackets as well as clear plastic or sapphire brackets.

Some examples of the prior art include U.S. Pat. Nos. 3,745,653 to Cohl; 4,063,360 to Walker; 4,411,625 to Koblitz et al.; 4,435,160 to Randklev; 4,340,528 to Lee, Jr. et al.; 3,250,003 to Collito; 4,180,911 to Bullock; and 4,179,812 to Wright.

SUMMARY OF THE INVENTION

This invention is directed to a method of bonding orthodontic brackets to teeth utilizing a visible and/or ultraviolet light curable polymer bonding agents which include a Bis—GMA resin reacted with an aliphatic diisocyanate, a diluent monomer and a photosensitizer which are blended with a filler of quartz, barium silicate or barium aluminum silicate, having particle sizes that average approximately 4 to 5 microns, together with an added pigment. The bonding agents are sufficiently viscous in an uncured state so that when they are applied to the base of an orthodontic bracket they retain the bracket in position on a tooth until such time as the bonding agents are polymerized using a primarily visible light source having a principle light emission in the range of between 360–500 nanometers. When opaque metal and ceramic brackets are used, the light is directed from at least two angles toward an area between the base of the bracket and the surface of the tooth thereby accomplishing complete polymerization of the bonding agents throughout the entire area of contact between the base and the tooth.

With the invention, clear ceramic, sapphire and plastic brackets, both small and large based, may be bonded to teeth using the aforementioned bonding agents and light source with the light source being applied directly through the bracket at right angles to the tooth facial surface.

It is the primary object of the present invention to provide a method of bonding perforate or imperforate, clear or opaque, metallic, ceramic, plastic or sapphire orthodontic brackets to teeth utilizing a photo polymerizable bonding agent and a technique which permits curing in generally less than twenty (20) seconds.

It is yet another object of the present invention to provide a method of applying orthodontic brackets to teeth wherein the bonding agent used is sufficiently viscous to retain the brackets in the desired position on the surface of the teeth until such time as the bonding agent is cured.

It is yet another object of the present invention to provide a method for bonding orthodontic brackets to teeth wherein the brackets may be securely bonded to the teeth by curing with a primarily visible light source for a period of approximately twenty seconds or less wherein the light is directionalized toward an area between the base of the bracket and the surface of the tooth when opaque or imperforate metallic brackers are used.

It is still another object of the present invention to provide a method for bonding orthodontic brackets to teeth wherein the base of the bracket may be of the smaller type and need not extend beyond the perimeter of the upper working portion of the brackets and therefore less tooth surface area is directly affected by the placement of the orthodontic brackets. Problems associated with tooth decay, tooth cleanup, following bracket removal, and appearance are thereby decreased.

It is a further object of the present invention to provide a method for bonding orthodontic brackets to teeth wherein the bond strength between the brackets and the teeth are significantly increased over priorly known bonding techniques with such increase in strength being accomplished with bonding agents which cure more quickly when exposed primarily to visible light although ultraviolet radiation may also be appropriate in some instances.

It is also an object of the present invention to provide a method of bonding orthodontic brackets to teeth which permits the brackets to be more easily removed following a patient's treatment and which makes cleanup of the surface of the teeth after such bracket removal more easily accomplished.

It is another object of the present invention to provide a method of bonding small based metal orthodontic brackets to teeth including those with mesh, dimpled or dovetailed features as well as to alternatively bond ceramic, sapphire or plastic brackets to teeth.

DESCRIPTION OF THE PREFERRED EMBODIMENT

As previously discussed, it is the purpose of the present invention to disclose a method for attaching orthodontic brackets to teeth in a manner which permits conventional small based brackets including those of the mesh, dimpled or dovetail type to be used with photopolymerizable bonding agents in a technique where bonding of the brackets may be accomplished within ten to twenty seconds or less by use of a primarily visible blue light source. Additionally, opaque or clear ceramic, plastic, sapphire and the newer reduced metal base brackets may also be bonded to teeth using the same photopolymerizable bonding agents and curing techniques. In an effort to give background into the difference between the types of orthodontic brackets which have been developed for use with various bonding agents, reference is made to FIGS. 1-3, 6 and 7 of the drawings.

Figure 1:
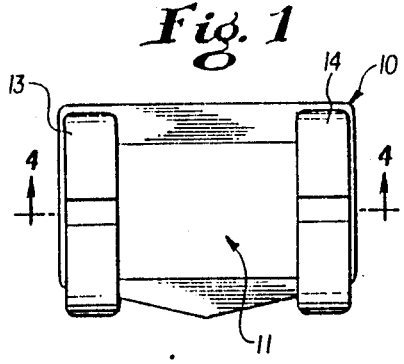
FIG. 1 is a top plan view of a conventional small base orthodontic bracket of the type which may be used with the method of the present invention.
Figure 2:
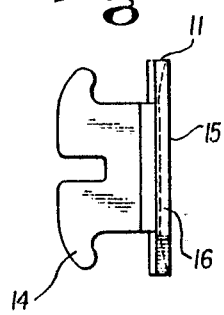
FIG. 2 is a right side view of the bracket of FIG. 1.
Figure 3:
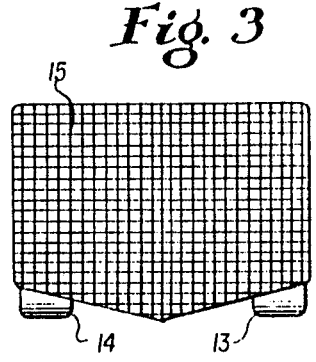
FIG. 3 is a bottom plan view of the orthodontic bracket of FIG. 1.
Figure 5:
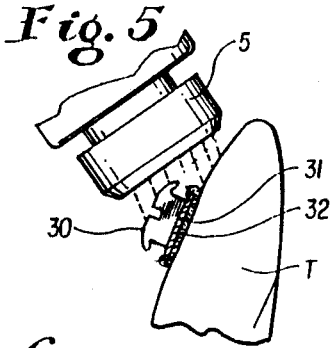
FIG. 5 is an illustration showing the placement of a clear plastic or sapphire bracket using the bonding technique in accordance with the present invention.

With specific reference to FIGS. 1-3, a conventional bracket 10 is disclosed having an imperforate opaque base portion 11 and a pair of upstanding wire engaging anchors 13 and 14. The type of orthodontic bracket disclosed in FIGS. 1-3 is similar to one manufactured by Ormco and includes a dimpled or meshed pad 15 which is braised to the base, as shown in FIG. 2, so as to form a generally concave undersurface 16. As noted from the top plan view of FIG. 1, the base portion with the underlying wire mesh braised thereto does not extend significantly beyond the wire anchors or wings 13 and 14. In this regard, the mounting portion of the bracket covers a minimal amount of tooth surface area as compared with the prior art orthodontic brackets shown in FIGS. 6 and 7. FIG. 5 is representative of a clear plastic or sapphire bracket.

In an effort to obtain quicker bonding time and stronger bonds between dental mounting brackets and teeth, photopolymerized bonding agents have been developed which are cured by the application of light or other radiation within a given wavelength. A problem encountered with such bonding agents is that the agent must be exposed to the light or radiation in order to be cured. In order to make it possible to use the stronger and more quickly cured photopolymers in fixing dental brackets to teeth, prior dental brackets were redesigned to include enlarged base or mounting portions. The enlarged base portions also had openings therethrough to permit light or other radiation to pass therethrough in order to cure a polymeric compound which was applied to the underside of the base and acted as the bonding agent for the bracket. Further, such bonding techniques have not resulted in strong bonds and have required curing times which are not as efficient as the present invention.

Figure 6:
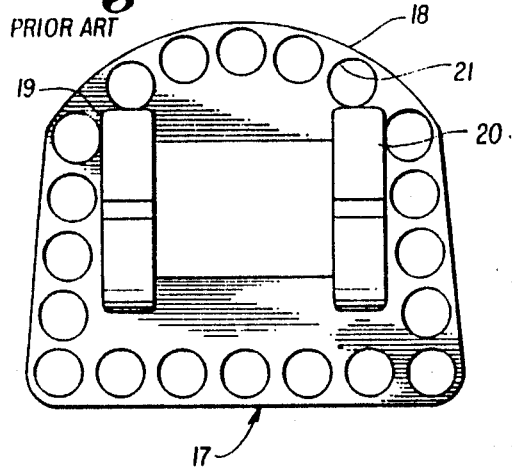
FIG. 6 is a top plan view showing a wide base bracket of the prior art.

In FIG. 6, a first type of enlarged base orthodontic bracket 17 is disclosed having a base portion 17 and a pair of upwardly extending wire engaging portions 19 and 20. Although the wire engaging portions 19 and 20 of this bracket are substantially the same dimension as those of the bracket shown in FIGS. 1-3, the base portion 17 extends well beyond the perimeter defined by the upstanding brackets 19 and 20. The outwardly extending base portion permits a plurality of openings 21 to be made around the periphery of the base. The openings permit a polymeric material to pass therethrough as the bracket is pushed against a tooth so that such polymeric material can be directly exposed to light waves or radiation being used to polymerize the polymeric bonding agent.

Figure 7:
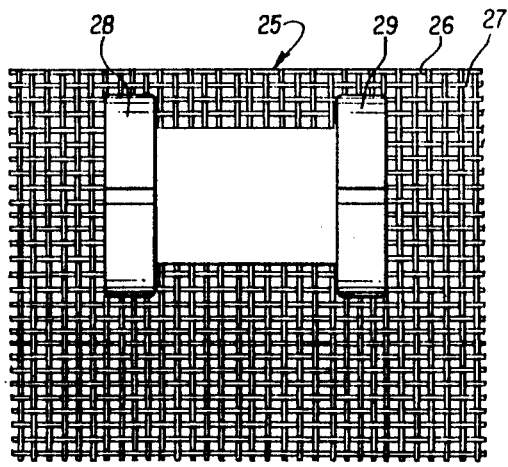
FIG. 7 is a top plan view showing another prior art wide base bracket.

In FIG. 7, another variation of an enlarged base dental bracket is identified as number 25. This dental bracket includes a base portion 26 which is identified by a wire mesh or screen which is shown as being generally rectangular in configuration (although other configurations including circular may be used) and having a plurality of openings 27 therein. A pair of upstanding wire engaging members 28 and 29 extend upwardly from the base and are of substantially the same size as the upstanding wire engaging flanges discussed with respect to the other dental brackets above. In this embodiment, it is noted that the wire mesh extends well beyond the area defined by the wire engaging portions of the bracket and thus covers a substantially greater area of tooth surface when applied for use. The wire mesh has the same function as the openings discussed with respect to the prior art structure shown in FIG. 6 and permits a polymeric material to be directly exposed therethrough to radiation or light being used to polymerize the same.

The use of photopolymerized or light activated bonding agents is generally preferred in that it permits a thicker composite bonding agent to be used than with the conventional bonding techniques. The thicker composite permits the orthodontic bracket to be positioned more accurately and retained in position until curing can be accomplished. The problem still exists, however, with prior art direct and indirect bonding techniques, that such bonding was not or could not be accomplished without increasing the width of the base of the brackets being used. The increase in bracket size has the disadvantages of covering a greater portion of the surface area of the tooth thereby being less desirable in appearance; requiring that more of the tooth area be cleaned after removal of the bracket; and further providing a larger perimeter area in which to trap food and other particles which may lead to surface damage of the tooth.

It has been found, however, that one type of photopolymerizable material offers significant advantages for attaching orthodontic brackets to teeth. This bonding agent includes a resin blend of Bis—GMA reacted with an aliphatic diisocyanate as the primary polymerizing agent. Bis—GMA being the common term for 2,2—bis [4-(2-hydroxy-3-methacryloxypropoxy) phenyl] propane.

The aliphatic diisocyanate is preferably a hexamethylene diisocyanate although other diisocyanates may be used such as other aliphatic and aromatic diisocyanates.

The resin binder compound is blended with a diluent monomer in order to achieve a viscosity of approximately 40,000 to 60,000 centipoise. The diluent monomers are chosen from photopolymerizable monomers including di and tri acrylates such as diethylene, triethylene, or ethylene glycol dimethacrylates and the like. Generally, the ratio of diluent monomer to resin being 1:6 to 1:1.

The binder resin compound and diluent monomer are then blended with a photosensitizing agent which consists of an alpha diketone photosensitizer, an amine reducing agent and an ultraviolet photosensitizer. The alpha diketone should be capable of initiating photopolymerization of the binder resin compound and may preferably be camphoroquinone which is present in an amount of between generally 0.10% to 0.25% by weight with the resin compound, monomer and photosensitizing agent. Benzil and other quinones including naphthoquinone may also be used.

The amine reducing agent need only be present in amounts by weight of 0.30% to 0.60% of the total resin binder, monomer and photosensitizing agent. Various trialkanolamines, and alkyldialkanolamines may be selected although the preferred are N-methyl-diethanolamines.

The ultraviolet photosensitizers are present in an amount of between 0.20% to 0.60% by weight of the resin compound, diluent monomer and photosensitizing agent. The ultraviolet sensitizers are selected from benzoin alkyl ethers and especially benzoin methyl, ethyl, isopropyl, and isobutyl ethers.

The above formulation which is a combination of the resin binder compound, diluent monomer and photosensitizing agent will hereinafter be referred to as a liquid bonding mixture. One commercially available liquid bonding agent having the foregoing composition is marketed under the name of Prisma-Bond, a product of L.D. Caulk Company.

The liquid bonding mixture is subsequently blended with a filler material of glass particles having sizes of less than 50 microns and preferably less than approximately 10–15 microns with the average being approximately 4–5 microns in order to form a bonding agent compound. The filler is selected from various silicates including barium silicate, and barium aluminum silicate. Quartz and the like may also be used. The filler material should preferably be silanated.

The appropriate pigment to match the color of the teeth being treated may be added to the bonding agent compound. Such pigments may be selected from a number of iron oxide or other acceptable dental pigments. The amount of the filler material may vary with the greater percentage of filler material added to strengthen the overall bonding agent. However, the increased amount of filler material also makes it more difficult to place the composite into the bracket mesh or base and manipulate the bracket prior to curing of the compound. Generally, the filler material should be present in the mixture from between 40–90% by weight, but preferably between the range of 70–85%.

When selecting the pigment, it should be noted that the lighter the pigment, the faster the curing or polymerization time that will be possible using the method of the invention.

A commercially available photopolymerizable bonding agent compound having the foregoing composition is distributed under the name of Prisma-Fil. Prisma-Fil is a known bonding agent distributed by the L.D. Caulk Company which is polymerized using a visible light having primary light emission waves in approximately the 360–500 nanometer range.

In preparing the teeth for application of a small imperforate base bracket using the photopolymerizable bonding agent compound and method of the present invention, it is first necessary that the surface of the teeth be cleaned such as using a prophy brush with a flour of pumice and water solution and then thoroughly rinsed and dried with compressed air. The surface to which the bracket is to be attached is then etched with a conventionally available etching solution and preferably with an etching solution of 50% phosphoric acid neutralized with 7% zinc oxide with applications being made for approximately sixty seconds after which the etching solution is rinsed thoroughly with water and the surface is dried. It should be noted that conventional etching solutions have strength equating to approximately 35%-37% phosphoric acid. Thereafter, the surface of the tooth is treated with the liquid bonding mixture discussed above which includes the resin bonding agent, diluent monomers and photosensitizing agent. Any excess liquid is then dried using compressed air. The bonding agent compound is then pressed into the base portion of the bracket in a manner to carefully insure that all voids are filled. An additional measure of compound or composite is then added to the previously placed thin layer of composite on the mesh base. Care should be taken when preparing the bracket to avoid, as much as possible, exposure of the bonding agent compound to the surrounding light.

The bracket with the bonding agent composite applied thereto is then placed on the prepared tooth surface and pressure is applied to expel the excess bonding agent compound or composite. The excess bonding agent compound is removed with a tool such as an explorer and the bracket positioned in the appropriate location. Additional pressure is subsequently applied to the bracket, after it is properly positioned, to insure intimate contact between the bracket base and the tooth surface and to expel any possible air or excess composite which may have been trapped therebetween.

It is extremely important that the second application of pressure be applied to force the bracket against the tooth after initial placement. The application of pressure may cause the resin mixture or bonding agent to lower the viscosity of the mixture thereby making the mixture flow better. The result of the second application of pressure will be: First, that a greater degree of agent bonding penetration is achieved with respect to the etched enamel surface of the tooth and the base of the bracket; and second, that a thinner layer of composite will be created between the bracket and tooth. Due to the viscosity of the bonding agent compound or composite, the bracket will not easily shift once it has been applied to the surface of the tooth thereby insuring that the bracket will not drift prior to curing of the bonding compound.

Figure 4:
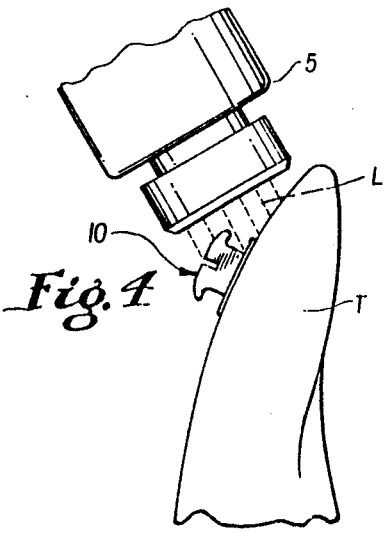
FIG. 4 is an illustration showing the placement of the light source adjacent the bracket and the tooth during polymerization when using an imperforate and opaque bracket.

Once the bracket has been applied to the tooth as discussed above, a source of visible light S having principle wave light emissions L in approximately the 360-500 nonometer range is brought in close proximity to the bracket and to the surface as shown in FIG. 4. Although the process preferably uses a light source in the visible range, a source having visible and/or ultraviolet radiation may be used in some instances. The light source is directed at two angles or placements between the base of the bracket and the surface of the tooth T. It has been found more preferable to direct the light source first along the occlusal aspect of the tooth bracket interface and thereafter directed at a second angle along the gingival aspect of the tooth bracket interface. However, the light could be directed from the mesial and distal aspects of the tooth bracket interface as well. It has been found during testing that the light should be directed from two spaced angles for a period of approximately ten seconds. Thereafter, the bracket will be bonded to the tooth with such bonding being complete throughout the width of the base even though the upper surface of the base is solid metal or opaque as shown in FIG. 1.

With particular reference to FIG. 5, the method of attaching orthodontic brackets in accordance with the present invention is also adaptable to permit plastic, sapphire, clear and ceramic bracket assemblies to be securely bonded to the surface of a tooth: In FIG. 5, a clear bracket 30 is shown as having a base portion 31 which is secured by a thin layer of bonding agent compound 32 to the surface of the tooth T. After the bonding agent is properly applied, a light source S is directed through the bracket to the tooth bracket interface, to thereby polymerize the bonding agent composite or compound.

In preparing a ceramic, sapphire, plastic or clear bracket assemblies for mounting to the surface of a tooth, the same steps as discussed with respect to the preferred embodiment are followed.

In an effort to make the brackets more appealing, manufacturers are currently marketing metal brackets having even smaller bases than those disclosed in FIGS. 1 through 3. Where it is necessary to increase the bond strength between the bracket and tooth interface because of the relatively small area of contact therebetween, a bead forming technique may be used to obtain additional bonding strength and improve the esthetic appearances as well. It should be noted, however, that due to the increased bond strength obtainable using the liquid bonding mixture and bonding agent compound and techniques discussed above, it is possible to secure small base brackets, such as those marketed under the name of Attract, to teeth and obtain strong and lasting bonds.

Prior to the concept of the method of the present invention, it was not believed possible to polymerize a bonding agent mixture or compound where such bonding agents were covered by a reflective metal or opaque imperforate surface It has been found, however, through testing, that not only do these photopolymerizable compounds cure when exposed to the proper light which is directed or aimed between the base of the bracket and the tooth but that the bonds created exceed the bonding strength normally achievable using other photopolymerizable or self-curing compounds and orthodontic bracket applying techniques.

In addition to the benefits obtained using the bonding agent mixture and compound and technique of the present invention, it has also been found that when a mesh based bracket, such as shown in FIG. 3, is removed from the tooth surface that the bonding agent has a tendency to be retained by the mesh material leaving little or no trace deposits of the compounds on the tooth. This makes it possible for the cleanup of the tooth surface to be more easily accomplished as very little composite or compound must be removed from the tooth.

From the foregoing, it can be seen that the method of applying orthodontic brackets in accordance with the teaching of the present invention permits the preferred small base brackets to be used thereby adding significantly to the enhanced appearance of the dental appliance and also reduces the affective area of the tooth which must be covered by the base of the brackets. In addition to the net affects achieved relative to the tooth surface, the present method permits an initial placement of the bracket on a tooth which placement will be insured by the viscosity of the uncured polymerizable compound. Polymerization and bonding of the bracket is thereafter quickly achieved in a period of approximately twenty seconds or less by directing an ultraviolet and/or visible light source from two aspects or sides of the tooth bracket interface thereby curing the bonding agent compound and bonding the bracket securely to the tooth surface. In addition to the foregoing, it has been determined that light sources having emissions principally in the 360-500 nanometer range, do not or are not known to cause irritation to the surrounding area of a patient's mouth, gum, eyes or skin, and are not harmful to the pulp of living human teeth.

I claim:

1. A method for bonding orthodontic brackets to teeth comprising the steps of:

cleaning the surface of the tooth in the area to which the bracket is to be applied;

etching the surface of the tooth and drying the etched area where the bracket is to be placed;

applying a photopolymerizable liquid bonding mixture to the etched area of the tooth;

applying a photopolymerizable bonding agent composite to the base of the bracket wherein the composite is sufficiently viscous in an uncured state to retain the bracket in position on the tooth when the bracket is applied thereto;

applying the base of the bracket to the etched area of the tooth by applying sufficient pressure to the bracket to expel composition therefrom;

insuring proper positioning of the bracket;

applying sufficient pressure to the bracket to insure the base is securely seated against the tooth and to expel any remaining excess composition or air from the tooth bracket interface to insure intimate contact at the tooth bracket interface;

directing a primarily visible light source from the bracket side of the tooth to the interface between the tooth and the base of the bracket to cure the bonding agent and securely fix the bracket to the tooth in a period of less than twenty seconds.

2. The method of claim 1 in which said light source has a primary emission in generally the 360-500 nanometer range.

3. The method of claim 1 in which said primarily visible light source is applied to the interface between the tooth and the base of the bracket for not more than approximately 10 seconds between each of two spaced aspects of the tooth bracket interface.

4. A method of bonding an orthodontic bracket having a base to a tooth utilizing a viscous composite comprising: p1 an inorganic filler and a photopolymerizable liquid bonding mixture which mixture includes a resin binder including bis-GMA reacted with a diisocyanate, a photosensitizing agent including an alpha diketone, and an amine reducing agent; the composite having a viscosity in an uncured state which is sufficient to retain the bracket in position on the tooth when the bracket is applied thereto; and;

cleaning the surface of the tooth in the area to which the bracket is to be applied;

etching the surface of the tooth and drying the etched area where the bracket is to be applied;

applying the viscous composite to the base of the bracket;

applying the base of the bracket to the etched area of the tooth by applying sufficient pressure to the bracket to expel composite therefrom;

insuring proper positioning of the bracket; thereafter, applying sufficient pressure to the bracket to insure the base is securely seated against the tooth and to expel any remaining excess composite or air from the tooth bracket interface to insure intimate contact at the tooth bracket interface; and directing a primarily visible light source from the bracket side of the tooth and to the interface between the tooth and the base of the bracket to cure the composite and securely adhere the bracket to the tooth.

5. The method of claim 4 including the additional step of applying the photopolymerizable liquid bonding mixture to the etched area of the tooth prior to applying the base of the bracket to the tooth.

6. The method of claim 5 including the additional step of cleaning off the excess bonding agent composite after applying the base of the bracket to the etched area of the tooth.

7. The method of claim 6 in which the primarily visible light source is directed to the interface between the tooth and the base of the bracket for a period of less than twenty seconds in order to cure the composite.

8. The method of claim 4 in which the primarily visible light source is directed to the interface between the tooth and the base of the bracket for a period of less than twenty seconds in order to cure the composite.

9. The method of claim 8 in which the light source is directed from two spaced aspects of the interface between the tooth and the base of the bracket.

* * * * *

REEXAMINATION CERTIFICATE (2104th)
United States Patent [19]
Nicholson

[11] B1 4,952,142
[45] Certificate Issued * Oct. 12, 1993

[54] METHOD OF BONDING ORTHODONTIC BRACKETS

[76] Inventor: James Nicholson, 128 S. 28th Ave., Hattiesburg, Miss. 39401

Reexamination Request:
No. 90/002,812, Aug. 17, 1992

Reexamination Certificate for:
Patent No.: 4,952,142
Issued: Aug. 28, 1990
Appl. No.: 199,755
Filed: May 27, 1988

[*] Notice: The portion of the term of this patent subsequent to Jun. 7, 2005 has been disclaimed.

Related U.S. Application Data

[63] Continuation-in-part of Ser. No. 691,101, Jan. 14, 1985, Pat. No. 4,749,352, which is a continuation-in-part of Ser. No. 632,931, Jul. 20, 1984, abandoned.

[51] Int. Cl.$^5$ .............................................. A61C 3/00
[52] U.S. Cl. .............................................. 433/9; 433/24
[58] Field of Search ................ 433/8, 9, 24; 523/116

[56] References Cited

U.S. PATENT DOCUMENTS

| | | | |
|---|---|---|---|
| 4,340,529 | 7/1982 | Lee, Jr. et al. | 524/105 |
| 4,457,818 | 7/1984 | Denyer et al. | 204/159 |
| 4,479,782 | 10/1984 | Orlowski et al. | 433/220 |
| 4,504,231 | 3/1985 | Koblitz et al. | 433/228 |

FOREIGN PATENT DOCUMENTS

290133  9/1988  European Pat. Off. .

OTHER PUBLICATIONS

Lee Pharmaceuticals Technical Bulletin, "Orthodontic Bracket Adhesive" No. 2100, May 1978.

*Primary Examiner*—John J. Wilson

[57] ABSTRACT

A method of direct or indirect bonding orthodontic brackets including metal, ceramic, sapphire, plastic and other clear brackets to teeth utilizing light curable polymer bonding agent compounds which are sufficiently viscous in an uncured state to retain a bracket in an applied position on the tooth until the bonding agent is cured and which bonding agents are curable within approximately twenty (20) seconds or less, by directing a visible and/or ultraviolet light source between the base of the bracket and the tooth to thereby thoroughly and securely bond the bracket to the tooth in the desired position. The method subsequently permits the bracket to be removed simultaneously with most of the bonding agent attached thereto thereby facilitating tooth cleaning following bracket removal.

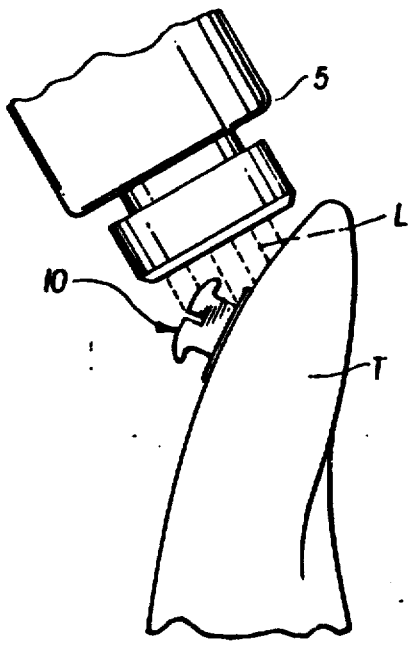

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS HAS BEEN DETERMINED THAT:

The patentability of claims 1-9 is confirmed.

* * * * *